US 6,611,576 B1

(12) United States Patent
Besser et al.

(10) Patent No.: US 6,611,576 B1
(45) Date of Patent: Aug. 26, 2003

(54) AUTOMATED CONTROL OF METAL THICKNESS DURING FILM DEPOSITION

(75) Inventors: Paul R. Besser, Austin, TX (US); Paul L. King, Mountain View, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 33 days.

(21) Appl. No.: 09/780,476

(22) Filed: Feb. 12, 2001

(51) Int. Cl.⁷ .............................................. G01N 23/223
(52) U.S. Cl. .............................................. 378/48; 378/50
(58) Field of Search .............................. 378/34, 35, 48, 378/50, 44, 45, 54, 88, 89

(56) References Cited

U.S. PATENT DOCUMENTS

| 4,169,228 A | | 9/1979 | Briska et al. ................. 378/45 |
| 4,764,945 A | * | 8/1988 | Abe ............................. 385/50 |
| 5,113,421 A | | 5/1992 | Gignoux et al. ............... 378/50 |
| 5,305,366 A | * | 4/1994 | Nakahara et al. ............. 378/45 |
| 5,657,363 A | | 8/1997 | Hossain et al. ................ 378/45 |
| 5,755,877 A | * | 5/1998 | Kamakura et al. ............ 117/85 |
| 6,349,128 B1 | * | 2/2002 | Nelson ......................... 378/44 |

* cited by examiner

*Primary Examiner*—Drew A. Dunn
*Assistant Examiner*—Therese Barber

(57) ABSTRACT

A novel method of automatically controlling thickness of a metal film during film deposition in a deposition chamber. The method involves producing an X-ray beam directed to the metal film deposited on a wafer in a deposition chamber, and detecting X-ray fluorescence of the metal film. The thickness of the metal film determined based on the detected X-ray fluorescence is compared with a preset value to continue deposition if the determined thickness is less than the preset value. Deposition is stopped when the determined thickness reaches the preset value.

7 Claims, 2 Drawing Sheets

AUTOMATED CONTROL OF METAL THICKNESS DURING FILM DEPOSITION

FIELD OF THE INVENTION

The present application relates to semiconductor device manufacturing, and in particular, to automatically controlling metal thickness during film deposition using X-ray fluorescence (XRF) detection.

BACKGROUND ART

During semiconductor device manufacturing, thin metal layers are deposited on semiconductor wafers to form vias, lines and various layers such as diffusion barriers, adhesion or seed layers, primary conductors, antireflection coatings, and etch stops. For example, sputter deposition, also known as physical vapor deposition (PVD), is widely used for the fabrication of metal thin-film structures on semiconductor wafers. Sputtering involves removing atoms from a solid material and then depositing the resultant vapor on a nearby substrate.

Sputter deposition is usually carried out in diode plasma systems known as magnetrons, in which the cathode is sputtered by ion bombardment and emits the atoms, which are then deposited on the wafer in the form of a thin film. Depending on the lithography scheme, these films are then etched by means of reactive ion etching (RIE) or polished using chemical-mechanical polishing (CMP) to help delineate circuit features.

The principal type of system currently used for high-rate deposition of metals, alloys, and compounds is known as the magnetron cathode system. This type of tool uses magnetic confinement of electrons in the plasma, which results in a higher plasma density than in either radio-frequency (rf) or direct-current (dc) diode systems. The higher plasma density reduces the discharge impedance and results in a much higher-current, lower-voltage discharge. As a rough example, an rf diode tool operating at 2 kW might have a peak-to-peak rf voltage of over 2000 V. A conventional magnetron system operated at 2 kW might have a dc discharge voltage of 400 V and an ion current of 5 A to the cathode.

Current manufacturing-scale magnetron systems are constructed from stainless steel. They are typically configured with cryopumps connected directly to their deposition chambers by means of large-diameter valves, and the resultant base pressure is generally in the low $10^{-8}$-Torr range for most cathodes, and in the $10^{-9}$-Torr range for Ti, for which the chemically active nature of the deposited films can contribute appreciably to the net pumping speed of the system.

The working pressure during sputtering is typically 0.5 to 30 mTorr, which requires a gas flow of many tens of standard cubic centimeters per minute (sccm). Because of base-pressure considerations, manufacturing-level systems are not baffled and therefore retain approximately the true base pressure of the chamber during deposition. The magnetron chambers used for large-scale semiconductor applications are configured as ports on an integrated-process load-locked tool, and wafers are introduced to the deposition chamber via a load lock Sputter deposition is managed by deposition time. The rate is calibrated against time, and then films are deposited for a fixed time period. However, due to process variations, thickness of deposited films for specific wafers or lots is hard to control during film deposition. Typically, metal film thickness is measured after deposition on some sampled wafers.

However, mechanical and electrical properties of fabricated semiconductor devices strongly depend on metal film thickness. Thickness variations greatly affect the device performance. Therefore, it would be desirable to control metal film thickness on every wafer during film deposition.

DISCLOSURE OF THE INVENTION

The present invention offers a novel method of monitoring a parameter of a metal film being deposited on a wafer during semiconductor device fabrication. The method involves producing an X-ray beam directed to a metal film during deposition of the metal film on the wafer in a deposition chamber, and detecting the X-ray fluorescence of the metal film to determine the required parameter of the film.

The determined parameter may be compared with a preset value to continue deposition of the metal film if the determined parameter differs from the preset value. Deposition of the metal film may be stopped when the determined parameter coincides with the preset value.

In accordance with one aspect of the present invention, thickness of a metal film being deposited on a wafer is automatically controlled during film deposition by producing an X-ray beam directed to the metal film, and detecting X-ray fluorescence of the film.

The thickness of the metal film determined based on the detected X-ray fluorescence may be compared with a preset value to continue deposition if the determined thickness is less than the preset value. Deposition may be stopped when the determined thickness reaches the preset value.

Still other aspects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DETAILED DESCRIPTION OF THE INVENTION

Figure 1:
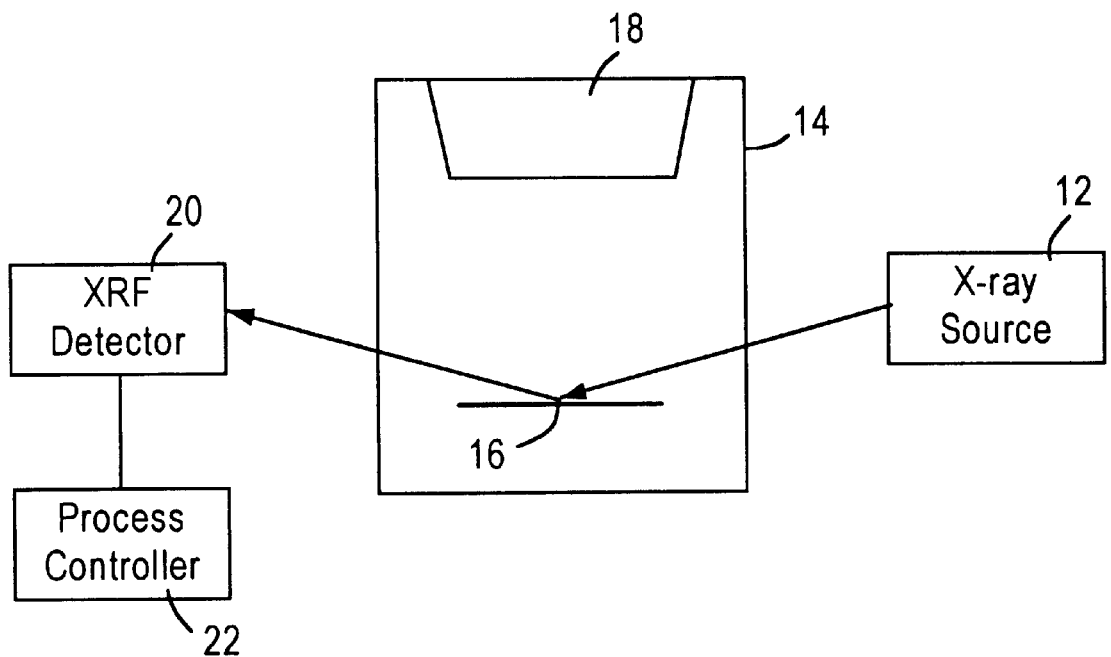
FIG. 1 schematically illustrates an exemplary control system for implementing the present invention.

Although the invention has general applicability for controlling metal thickness during various deposition processes, such as CVD, PVD, PECVD, etc, a preferred embodiment of the invention is disclosed with an example of sputter deposition of metal films. FIG. 1 schematically illustrates an exemplary automated system 10 for controlling metal thickness of the present invention. The system 10 enables controlling deposition of such metals as Ni, Co, Al, Ti, TiN, W and Cu on a wafer placed in a deposition chamber.

In accordance with one aspect of the present invention, the thickness of a metal film being deposited on a wafer is controlled using X-ray fluorescence (XRF). The XRF effect is based on irradiating a sample with an unfiltered beam of X-rays. If a beam of sufficiently short-wavelength X-radiation is employed, a characteristic X-spectra can be observed from the excited sample. X-ray fluorescence occurs when electrons absorb X-radiation raising them to a higher orbit, and the energized electrons then drop down through a series of steps to lower energy states. This process results in the release of photons at lower energy states. The resulting intensities of fluorescent X-rays are smaller by a factor of nearly 1000 times than intensities of the X-ray beam obtained from direct excitation with a beam of electrons.

The system 10 includes an X-ray source 12 emitting a beam of X-rays appropriate for the XRF detection. An X-ray tube may be employed as the X-ray source 12. Typical X-ray tube comprises a heavy metal head that confines the X-radiation, a thin beryllium window and a reentrant glass envelope that retains the vacuum. The head contains the tungsten filament heated to incandescence by an electric current to emit electrons that are focused on a concave focusing electrode and accelerated to the anode operating at a high positive potential. The anode consists of a thin plating of the metal imbedded on a heavy copper block, which conducts heat away from the focal point. This focal point is bombarded by the filament electrons and is the source of the X-rays. The X-rays are emitted in all directions but emerge from the metal head through the beryllium window.

The X-ray source 12 is arranged near or inside a sputter chamber 14 used for performing deposition of a metal film on a wafer 16. For example, the PVD deposition may be employed. A sputter target 18 arranged in the sputter chamber 14 is bombarded by argon ions that remove atoms from a solid material of the target 18. The resultant vapor is deposited on the wafer 16. In addition to the target material, the target 18 may include the copper backing plate. A magnetron cathode consisting of an array of powerful permanent magnets may be placed behind the target 18. The magnets create a magnetic field across the face of the target to trap electrons.

The argon ions responsible for target erosion may be created by a glow-discharge plasma generator that uses the target as the cathode, and the sputter chamber wall or some other electrode as the anode. A voltage is developed across these electrodes to accelerate free electrons, which impact gas molecules to create ions, more free electrons, free radicals and molecules in excited states. The latter can spontaneously relax to their ground states generating photons. Once created, these particles diffuse out of plasma toward the target.

The X-ray source 12 is installed so as to direct the X-ray beam toward the metal film being deposited. The X-ray beam causes the metal film to emit characteristic fluorescent lines. An XRF detector 20 is arranged in or near the sputter chamber 14 to detect the X-ray fluorescence. Collimators may be used to intercept divergent X-rays and direct a parallel beam to the detector's window. If the X-ray source 12 and the XRF detector 20 are installed outside of the sputter chamber 14, X-ray transparent windows may be made in the sputter chamber 14 to allow X-ray beams produced by the X-ray source 12 to pass to the metal film, and to allow X-ray fluorescence emitted by the meal film to pass to the XRF detector 20.

For example, a solid-state semiconductor XRF detector may be used for detecting the X-ray fluorescence emitted by the metal film being deposited on the wafer. The solid-state XRF detector 20 may be a lithium drifted detector consisted of silicon single crystal semiconductor with a region formed by diffusing lithium into p-type silicon or germanium. This region is sandwiched between p-type and n-type regions. The lithium drifted XRF detector need to be maintained at liquid nitrogen temperature because of lithium's extremely high diffusion rate.

A large number of electron-hole pairs in the semiconductor are produced each time an incident X-ray photon is absorbed. A low-noise, high-gain preamplifier may be used to amplify the detection signal produced by the detector. Those skilled in the art will recognize that a gas-filled XRF detector or a photoelectric XRF detector also may be used as the XRF detector 20.

The X-ray fluorescence of the metal film indicates various parameters of the metal film including the film thickness. The XRF detector 20 produces an output signal representing the X-ray fluorescence of the meatal film. For example, the XRF detector 20 may be pre-calibrated to produce predetermined output values in response to preset values of the film thickness for particular metals being deposited. The output signal of the XRF detector 20 is supplied to a process controller 20 that controls the sputter deposition of the metal thin film. The controller 20 may be implemented as a specifically engineered chip having logic circuits and other components for performing the functions described below. Alternatively, the controller 20 may be implemented using a general-purpose digital signal processor and appropriate programming.

Figure 2:
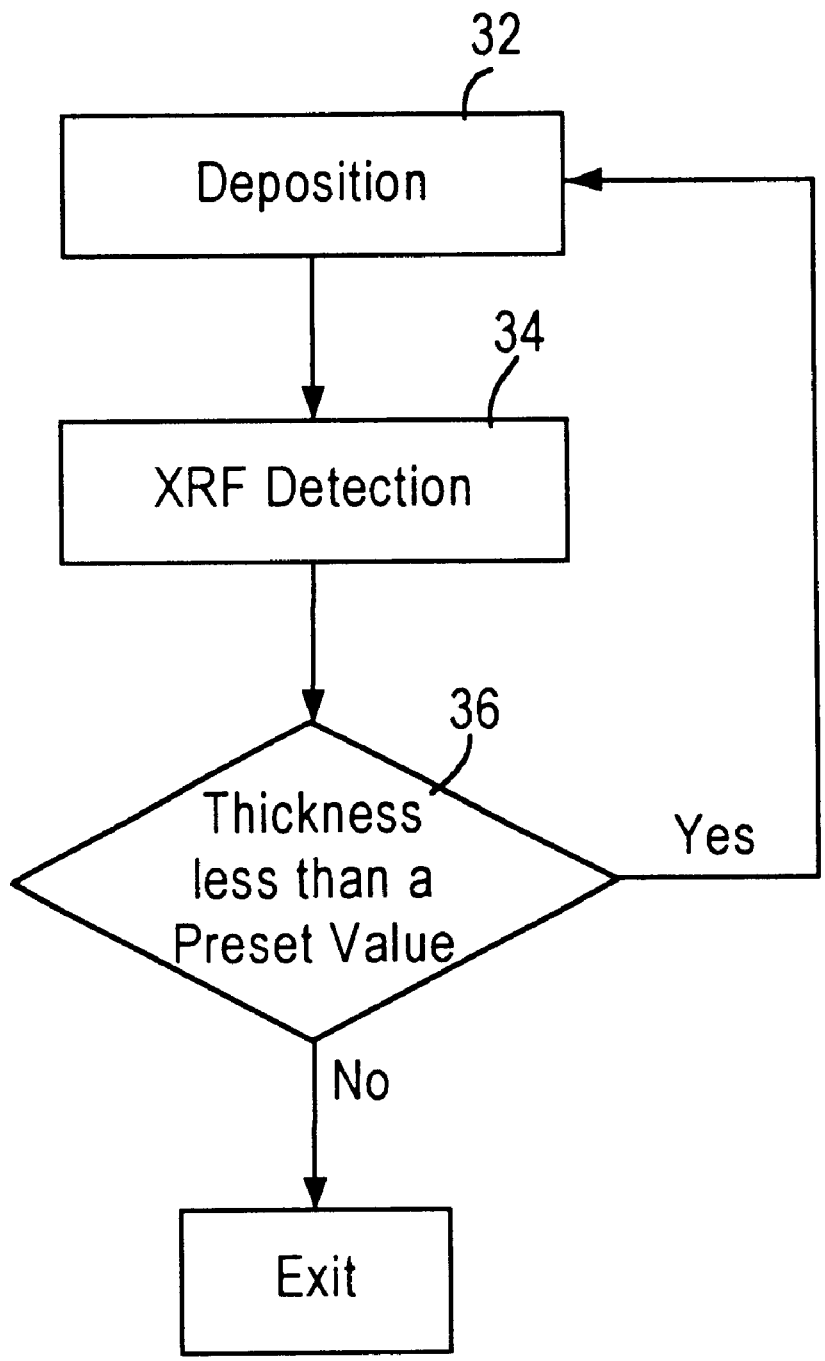
FIG. 2 is a flow chart illustrating a method of automatically controlling metal thickness of the present invention.

A flow chart in FIG. 2 illustrates the method of controlling metal film thickness in accordance with the present invention. During sputter deposition of a metal film on a wafer installed in the sputter chamber 14 (block 32), the X-ray source 12 emits an X-ray beam directed to the metal film. The XRF detector 20 detects the X-ray fluorescence emitted by the metal film irradiated with the X-ray beam (block 34). The output signal of the XRF detector 20 representing the thickness of the metal film is supplied to the controller 22 that determines the thickeners of the metal film, and compares the detected thickness with a preset value.

If the controller 22 determines that the thickness of the metal film is less than a preset value (block 36), it controls the sputter deposition process to continue metal film deposition. When the controller 22 determines that the thickness of the metal film reaches the preset value, it stops the deposition process.

Accordingly, the present invention enables automatic in-situ control of metal film thickness on every wafer during film deposition to deposit a metal film having required thickness.

Those skilled in the art will recognize that the present invention admits of a number of modifications, within the spirit and scope of the inventive concepts. For example, as discussed above, the X-ray source 12, the XRF detector 20 and the process controller 22 may be implemented in a number of different ways. The chamber 14 may be any chamber or furnace for performing any type of film deposition such as PVD, CVD, or PECVD to provide deposition of such metals as Ni, Co, Al, Ti, TiN, W and Cu. In this disclosure, there are shown and described only the preferred embodiments of the invention, but it is to be understood that the invention is capable of changes and modifications within the scope of the inventive concept as expressed herein.

What is claimed is:

1. Method of monitoring a parameter of a metal film being deposited on a semiconductor wafer, the method comprising the steps of:

producing an X-ray beam directed to the metal film during deposition of the metal film on the wafer in a deposition chamber, detecting X-ray fluorescence of the metal film to determine the parameter of the metal film, and comparing the determined parameter with a preset value to continue deposition of the metal film if the determined parameter differs from the preset value.

2. The method of claim 1, wherein the X-ray fluorescence of the metal film is detected for controlling thickness of the metal film being deposited on the wafer.

3. The method of claim 1, wherein deposition of the metal film is stopped if the determined parameter coincides with the preset value.

4. The method of claim 1, wherein deposition of the metal film is performed using sputter deposition.

5. Method of automatically controlling thickness of a metal film being deposited on a semiconductor wafer, the method comprising the steps of:

producing an X-ray beam directed to the metal film during deposition of the metal film on the wafer in a deposition chamber, determining the thickness of the metal film based on detected X-ray fluorescence of the metal film, and comparing the determined thickness of the metal film with a preset value to continue the deposition of the metal film if the determined thickness is less than the preset value.

6. The method of claim 5, wherein the deposition of the metal film is stopped if the determined thickness reaches the preset value.

7. The method of claim 5, wherein the metal film is deposited using sputter deposition.

* * * * *